(12) United States Patent
Leuthardt et al.

(10) Patent No.: US 12,017,075 B2
(45) Date of Patent: Jun. 25, 2024

(54) SYSTEMS AND METHODS FOR STIMULATING SYMPATHETIC NERVOUS SYSTEM

(71) Applicant: Washington University, St. Louis, MO (US)

(72) Inventors: Eric Leuthardt, St. Louis, MO (US); Daniel Moran, St. Louis, MO (US); Matthew MacEwan, St. Louis, MO (US); Amy Moore, St. Louis, MO (US); Paige Cloonan, St. Louis, MO (US); Yidan Qin, St. Louis, MO (US); Christopher Zhang, St. Louis, MO (US); Ashwin Kamath, St. Louis, MO (US); Wilson Ray, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/690,493

(22) Filed: Mar. 9, 2022

(65) Prior Publication Data

US 2022/0193417 A1 Jun. 23, 2022

Related U.S. Application Data

(63) Continuation of application No. 16/415,311, filed on May 17, 2019, now Pat. No. 11,351,381.
(Continued)

(51) Int. Cl.
*A61N 1/36* (2006.01)
*A61N 1/05* (2006.01)
*A61N 1/378* (2006.01)

(52) U.S. Cl.
CPC ....... *A61N 1/36178* (2013.01); *A61N 1/0558* (2013.01); *A61N 1/378* (2013.01)

(58) Field of Classification Search
CPC ............ A61N 1/36; A61N 1/05; A61N 1/378
(Continued)

(56) References Cited

U.S. PATENT DOCUMENTS

| 4,573,481 A | 3/1986 | Bullara |
| 5,292,252 A | 3/1994 | Nickerson et al. |

(Continued)

FOREIGN PATENT DOCUMENTS

WO 2017192892 A1 11/2017

OTHER PUBLICATIONS

Gandhi, K. R., et al. "The morphology of lumbar sympathetic trunk in humans: a cadaveric study." Folia Morphol, 72(3):217-222 (2013).
(Continued)

*Primary Examiner* — Nadia A Mahmood
(74) *Attorney, Agent, or Firm* — Armstrong Teasdale LLP

(57) ABSTRACT

A system for stimulating a sympathetic chain includes an electrode assembly that is configured to attach to a bone in proximity to a targeted portion of the sympathetic chain. The electrode assembly includes a cathode and an anode. The system also includes a power supply connected to the electrode assembly and configured to deliver power to the electrode assembly. The electrode assembly generates an electrical field between the cathode and the anode when power is delivered to the electrode assembly. The electrical field reaches the targeted portion of the sympathetic chain to provide electrical stimulation to the targeted portion of the sympathetic chain.

24 Claims, 13 Drawing Sheets

Related U.S. Application Data

(60) Provisional application No. 62/673,416, filed on May 18, 2018.

(58) Field of Classification Search
USPC .......................................................... 607/42
See application file for complete search history.

(56) References Cited

U.S. PATENT DOCUMENTS

| | | | |
|---|---|---|---|
| 6,034,295 | A | 3/2000 | Rehberg et al. |
| 6,605,089 | B1 | 8/2003 | Michelson |
| 6,885,888 | B2 | 4/2005 | Rezai |
| 7,395,119 | B2 | 7/2008 | Hagen et al. |
| 7,431,734 | B2 | 10/2008 | Danoff et al. |
| 7,477,945 | B2 | 1/2009 | Rezai et al. |
| 7,615,070 | B2 | 11/2009 | Biscup |
| 8,024,048 | B2 | 9/2011 | Schroeppel et al. |
| 8,380,319 | B2 * | 2/2013 | Berger ............... A61B 17/8685 607/51 |
| 8,532,793 | B2 | 9/2013 | Morris et al. |
| 8,583,229 | B2 | 11/2013 | Rezai et al. |
| 8,634,921 | B2 | 1/2014 | Chavan et al. |
| 8,903,502 | B2 | 12/2014 | Perryman et al. |
| 2002/0116030 | A1 * | 8/2002 | Rezai .................... A61N 1/326 607/9 |
| 2004/0243207 | A1 | 12/2004 | Olson et al. |
| 2006/0276870 | A1 | 12/2006 | McGinnis |
| 2008/0125637 | A1 | 5/2008 | Geist et al. |
| 2009/0054951 | A1 | 2/2009 | Leuthardt et al. |
| 2010/0204766 | A1 | 8/2010 | Zdeblick et al. |
| 2010/0298886 | A1 | 11/2010 | Kraus et al. |
| 2013/0073000 | A1 | 3/2013 | Chavan et al. |
| 2013/0310901 | A1 * | 11/2013 | Perryman .............. A61N 1/025 607/117 |
| 2014/0046407 | A1 | 2/2014 | Ben-Ezra et al. |
| 2014/0200616 | A1 | 7/2014 | Leuthardt et al. |
| 2014/0330329 | A1 | 11/2014 | Thompson-Nauman et al. |
| 2014/0330334 | A1 | 11/2014 | Errico et al. |
| 2017/0173340 | A1 | 6/2017 | Gupte et al. |

OTHER PUBLICATIONS

Ogbonnaya, S. et al., "Vagal nerve stimulator: Evolving trends," Journal of Natural Science, Biology and Medicine, 4(1): 8-13 (2013).

NIH, "Peripheral Neuropathy Fact Sheet" Prepared by Office of Communications and Public Liaison, National Institute of Neurological Disorders and Stroke, National Instutes of Health, Bethesda, MD, 2019 (14 pages).

Pimenta, E. et al., "Resistant Hypertension, Incidence, Prevalence, and Prognosis," Circulation, 125(13): 1594-1596 (2012).

Rattay, Frank. "Analysis of models for extracellular fiber stimulation," IEEE Transactions on Biomedical Engineering 36(7): 676-682 (1989).

Cyberonics, "VNS Therapy-Frequently Asked Questions" An Introduction to VNS Therapy, downloaded from https://us.ivanova.cyberonics.com/sites/vnstherapy.com/files/Introduction-to-VNS-Therapy-English.pdf, Sep. 2019, (26 pages).

Cyberonics, "VNS Therapy® System Physician's Manual" www.livanova.com, Apr. 2019 (163 pages).

Cyberonics, "How VNS Therapy Works," downloaded from https://us.livanova.cyberonics.com/learn-more/how-it-works, LivaNova (2019).

* cited by examiner

SYSTEMS AND METHODS FOR STIMULATING SYMPATHETIC NERVOUS SYSTEM

CROSS-REFERENCE TO RELATED APPLICATIONS

This application is a continuation application of U.S. patent application Ser. No. 16/415,311 filed May 17, 2019. U.S. patent application Ser. No. 16/415,311 claims the benefit of U.S. Provisional Patent Application Ser. No. 62/673,416, filed May 18, 2018, the entire contents of which are incorporated herein by reference.

BACKGROUND

The present disclosure relates generally to stimulating the sympathetic nervous system and, more particularly, to a stimulation system including an electrode assembly that is capable of generating an electrical field for stimulating the sympathetic nervous system without direct physical contact with the sympathetic nervous system.

The sympathetic nervous system is a portion of the autonomic nervous system responsible for regulating organ system activity without conscious control. The sympathetic nervous system includes a sympathetic chain extending longitudinally along two sides of the spine from a cervical region through a lumbar portion of the spine. The sympathetic chain acts as a meeting location of the preganglionic nerve and the postganglionic nerve and extends to sympathetic fibers that innervate effector organs. Dysfunction of the sympathetic chain may cause diseases and conditions such as asthma, hypertension, hyperhidrosis, gastrointestinal disease, and overactive bladder syndrome. In addition, peripheral neuropathy caused by damage to nerve axons or myelin sheaths of the sympathetic chain can lead to recurring and/or chronic neuropathic pain.

Accordingly, stimulation or inhibition of the sympathetic chain may be used to treat a number of conditions. However, stimulation of the entire sympathetic chain or an incorrect portion of the nervous chain may not treat the condition and may cause additional conditions associated with dysfunction of the sympathetic nervous system. In addition, typical nerve stimulation systems, such as systems for stimulating the vagus nerve, require contact with the targeted nerve. However, contact with the sympathetic chain could damage the sympathetic chain. Moreover, it may be difficult to access the sympathetic chain to position the stimulation system because the sympathetic chain is positioned in proximity to the spine.

It is desirable, therefore, to provide a system for stimulating targeted portions of the sympathetic nervous system with reduced risk of damage to the sympathetic nervous system.

BRIEF DESCRIPTION

In one aspect, a system for stimulating a sympathetic chain includes an electrode assembly that is configured to attach to a bone in proximity to a targeted portion of the sympathetic chain. The electrode assembly includes a cathode and an anode. The system also includes a power supply connected to the electrode assembly and configured to deliver power to the electrode assembly. The electrode assembly generates an electrical field between the cathode and the anode when power is delivered to the electrode assembly. The electrical field reaches the targeted portion of the sympathetic chain to provide electrical stimulation to the targeted portion of the sympathetic chain.

In another aspect, a method of stimulating a sympathetic chain includes positioning an electrode assembly within a body of an animal. The method also includes attaching the electrode assembly to a bone in proximity to a targeted portion of the sympathetic chain. The electrode assembly includes a cathode and an anode. The method further includes connecting a power supply to the electrode assembly and connecting a controller to the power supply. The power supply is configured to deliver power to the electrode assembly. The electrode assembly generates an electrical field between the cathode and the anode when power is delivered to the electrode assembly. The method also includes providing electrical stimulation to the targeted portion of the sympathetic chain via the electrical field. The controller is configured to control power supplied to the electrode assembly and control electrical stimulation provided to the targeted portion of the sympathetic chain.

In yet another aspect, an electrode assembly for stimulating a sympathetic chain includes a support structure, an anode, and a cathode. The support structure is configured to attach to a bone in proximity to a targeted portion of the sympathetic chain. The anode and cathode are attached to the support structure. The electrode assembly generates an electrical field between the cathode and the anode when power is delivered to the electrode assembly. The electrical field reaches the targeted portion of the sympathetic chain to provide electrical stimulation to the targeted portion of the sympathetic chain.

DETAILED DESCRIPTION

As used herein, the term "tissue" refers to a cellular structure performing a specific function in an animal. The terms "stimulate", "stimulating", and "stimulation" refer to externally influencing tissue to affect a characteristic of the tissue. Accordingly, stimulating tissue may include exciting and/or inhibiting a function of the tissue. The term "animal" refers to a multicellular organism capable of voluntary movement. For example, animals include, without limitation, humans, horses, dogs, cats, mice, and rats. Thus, the implants, systems and methods disclosed herein are suitable for use in animals including, but not limited to, humans, horses, dogs, cats, mice, and rats.

Embodiments of a system for stimulating sympathetic nerves include an implantable electrode assembly. The electrode assembly is an implantable medical device capable of delivering electrical stimulation to nerves. The electrode assembly includes an anode and a cathode and generates an electrical field between the anode and the cathode. The electrode may be positioned such that the electrical field encompasses a targeted portion of the sympathetic chain. A power supply delivers electrical current to the electrode assembly to cause the electrode assembly to provide therapeutic electrical stimulation to the targeted portion of the sympathetic chain via the electrical field. As a result, the system provides electrical stimulation to the sympathetic nerve without direct physical contact with the sympathetic nerve. Moreover, the electrode assembly may be secured to a bone or other structure within the body in an accessible position that reduces potential complications during a surgical procedure to implant the electrode within the body. In addition, the electrode assembly may be precisely positioned in proximity to the sympathetic chain without directly contacting the nervous tissue by securing the electrode assembly to a bone.

Figure 1:
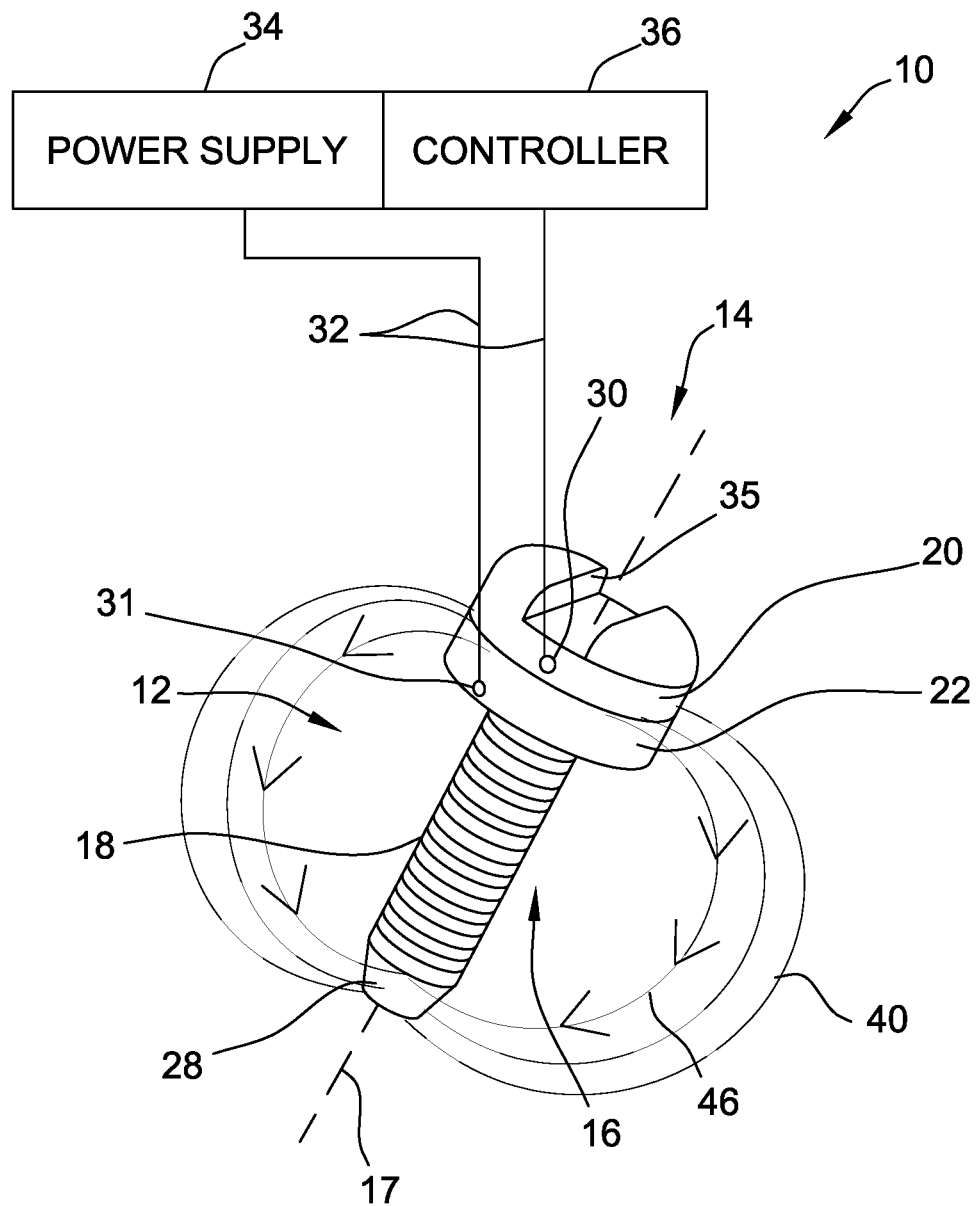
FIG. 1 is a schematic view of a system for stimulating a sympathetic chain.
Figure 2:
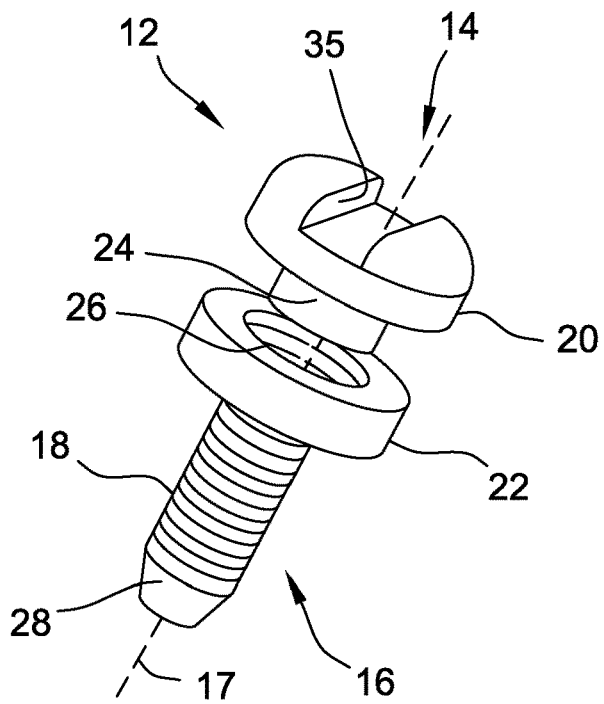
FIG. 2 is a perspective view of an electrode assembly for use with the system shown in FIG. 1, with a portion of a head detached from a stem of the electrode assembly.
Figure 3:
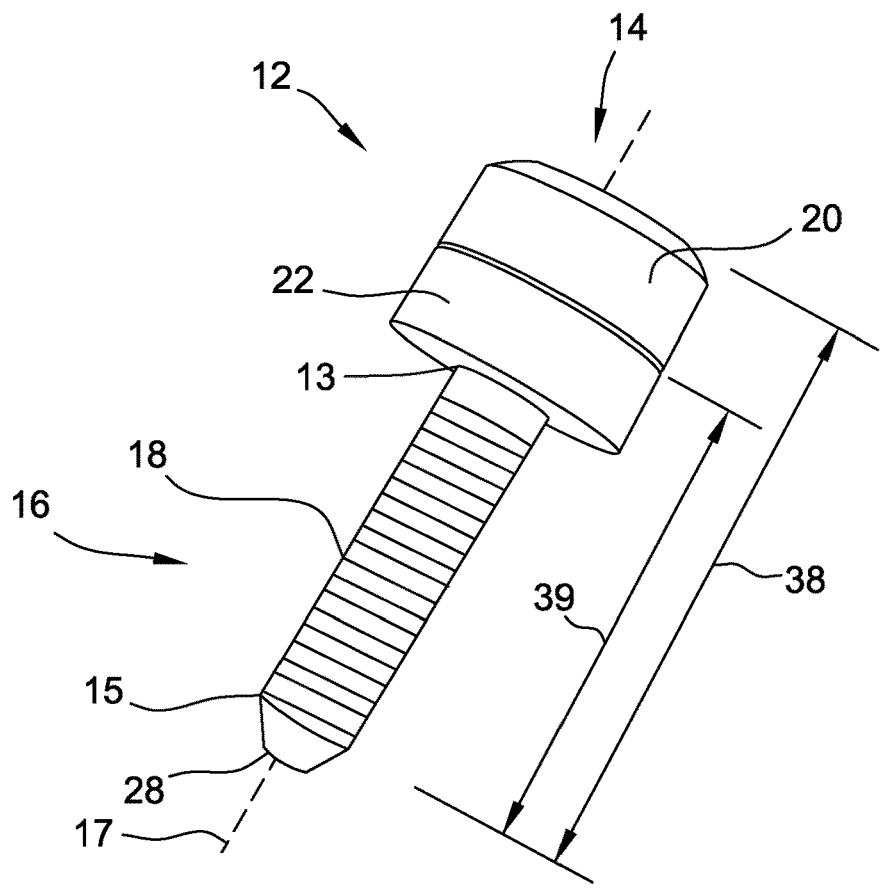
FIG. 3 is a side view of the electrode assembly shown in FIG. 2.

FIG. 1 is a schematic view of a system 10 for stimulating a sympathetic nervous system. FIG. 2 is a perspective view of an electrode assembly 12 of the system 10. FIG. 3 is a side view of the electrode assembly 12. The electrode assembly 12 is configured to be implanted within a body of an animal and deliver electrical stimulation to tissue such as sympathetic nerves without contacting the tissue. The electrode assembly 12 includes a head 14 and a stem 16. The stem 16 includes a threaded body 18. The threaded body 18 is a cylinder with a helical thread that extends along a longitudinal axis 17. In the illustrated embodiment, the electrode assembly 12 is in the form of a bone screw. In other embodiments, the electrode assembly 12 may have any configuration that enables the system 10 to operate as described herein.

The head 14 includes an anode 20 and a rim 22. In the illustrated embodiment, the head 14 is substantially cylindrical with a rounded end forming the anode 20. In suitable embodiments, the anode 20 and the rim 22 may be formed as separate pieces and connected together. For example, in the illustrated embodiment, the anode 20 includes a threaded stem 24 that is matingly received in a bore 26 in the rim 22. The head 14 may include a groove 35 or other feature to allow the electrode assembly 12 to be rotated using a tool. In suitable embodiments, the head 14 may be generally shaped to correspond to the shape of the tool and enable the tool to rotate the electrode assembly 12. In other embodiments, the electrode assembly 12 may include any head 14 that enables the electrode assembly 12 to function as described herein.

The stem 16 is attached to the head 14 at a proximal end 13 and extends from the head 14 along the longitudinal axis 17. The stem 16 includes a cathode 28 on a distal end 15 opposite the head 14. Accordingly, the cathode 28 and the anode 20 are located at opposite ends of the electrode assembly 12 and are spaced apart by substantially the entire length of the electrode assembly 12. In suitable embodiments, each of the cathode 28 and the anode 20 may be placed in any suitable configuration on the electrode assembly 12 such that the cathode 28 and the anode 20 may be spaced apart by any suitable distance, for example the cathode 28 and the anode 20 may be positioned at either end of the electrode assembly 12 or in a middle of the electrode assembly 12.

The electrode assembly 12 has a length 38 measured along the longitudinal axis 17. Also, the cathode 28 and the anode 20 are separated by a distance 39. In this illustrated embodiment the distance 39 is substantially equal to the length 38 because the cathode 28 and the anode 20 are positioned on opposite ends of the electrode assembly 12. The length 38 is configured for the anode 20 and the cathode 28 to generate an electrical field 40 therebetween. For example, the length 38 may be in a range of about 4 millimeters (mm) to about 22 mm. The length 38 may enable the electrical field 40 to have a range that encompasses a targeted tissue when the electrode assembly 12 is positioned proximate the tissue. In addition, the length 38 may allow the electrode assembly 12 to be modular and secured to different bones or body structures in multiple applications. As a result, a surgeon is not required to select from a number of electrode assemblies 12 having different lengths for specific applications. In other embodiments, the electrode assembly 12 may have any length that enables the electrode assembly 12 to function as described herein.

The threaded body 18 and the rim 22 are coated in an electrically insulative material, i.e., a material with an electrical conductivity less than $10^{-8}$ Siemens per centimeter (S/cm) at 25° C., to insulate the electrode assembly 12 from the environment and inhibit current from flowing to the environment when electrical current is provided to the electrode assembly 12. For example, the threaded body 18 and/or the rim 22 may be coated with titanium dioxide ($TiO_2$). In other embodiments, the threaded body 18 and the rim 22 may include any materials that enable the electrode assembly 12 to function as described herein. For example, in suitable embodiments, the threaded body 18 and/or the rim 22 may be at least partially constructed from non-conductive materials.

The anode 20 and the cathode 28 are coated in an electrically conductive material, i.e., a material with an electrical conductivity greater than $10^3$ S/cm at 25° C., to facilitate the conductance of electrical current between the environment and the anode 20 and the cathode 28. For example, the anode 20 and the cathode 28 may be coated in titanium nitride (TiN). In other embodiments, the anode 20 and the cathode 28 may include any materials that enable the electrode assembly 12 to operate as described herein.

With reference to FIG. 1, the electrode assembly 12 receives power from a power supply 34 through wires 32. The wires 32 are connected to the anode 20 and the cathode 28. For example, one of the wires 32 extends through an opening 30 defined by the anode 20 and into the anode 20. Another one of wires 32 extends through an opening 31 defined by the rim 22 and through an internal channel (not shown) defined by the stem 16. The wire 32 extends through the rim 22 and the threaded body 18 to the cathode 28. When electrical current is provided to the electrode assembly 12 from the power supply 34, the anode 20 and the cathode 28 generate an electrical field to provide electrical stimulation to targeted tissue of the human body at the location in which the electrode is implanted. In suitable embodiments, the electrode assembly 12 includes electronics configured to control amplitude and duration of the electrical stimulation provided to the targeted tissue.

A controller 36 regulates electrical current provided to the electrode assembly 12. In suitable embodiments, the controller 36 may be integrated into the power supply 34. The controller 36 may include, for example and without limitation, a processor, a capacitor, an amplifier, and a waveform generator. The waveform generator generates electrical waveforms to provide a desired current through the wires 32 to the electrode assembly 12. The electrode assembly 12 is configured to generate therapeutic electrical pulses based on electrical current received from the power supply 34. For example, the controller 36 may provide a current having a desired amplitude and frequency based on the targeted tissue and a desired treatment. In other embodiments, the controller 36 and the electrode assembly 12 may communicate in any manner that enables the system 10 to operate as described herein. For example, in suitable embodiments, the controller 36 and the electrode assembly 12 may communicate wirelessly. In such embodiments, the controller 36 may be configured to control the electrode assembly 12 from the exterior of the body by transmitting electrical signals through at least a portion of the body. In addition, the power supply 34 and the controller 36 may be configured to deliver power wirelessly to the electrode assembly 12.

During operation, electrical current is provided from the power supply 34 to the electrode assembly 12 through the wires 32. When the electrical current flows through the wires 32 to the electrode assembly 12, the electrical current is transmitted between the cathode 28 and the anode 20 to generate an electrical field 40. The electrical field 40 may have a range that encompasses a targeted tissue when the electrode is positioned proximate the tissue such that electrical stimulation is provided to the tissue. The amplitude and frequency of the electrical current provided to the electrode assembly 12 may be controlled to provide therapeutic pulses to the tissue.

Figure 4:
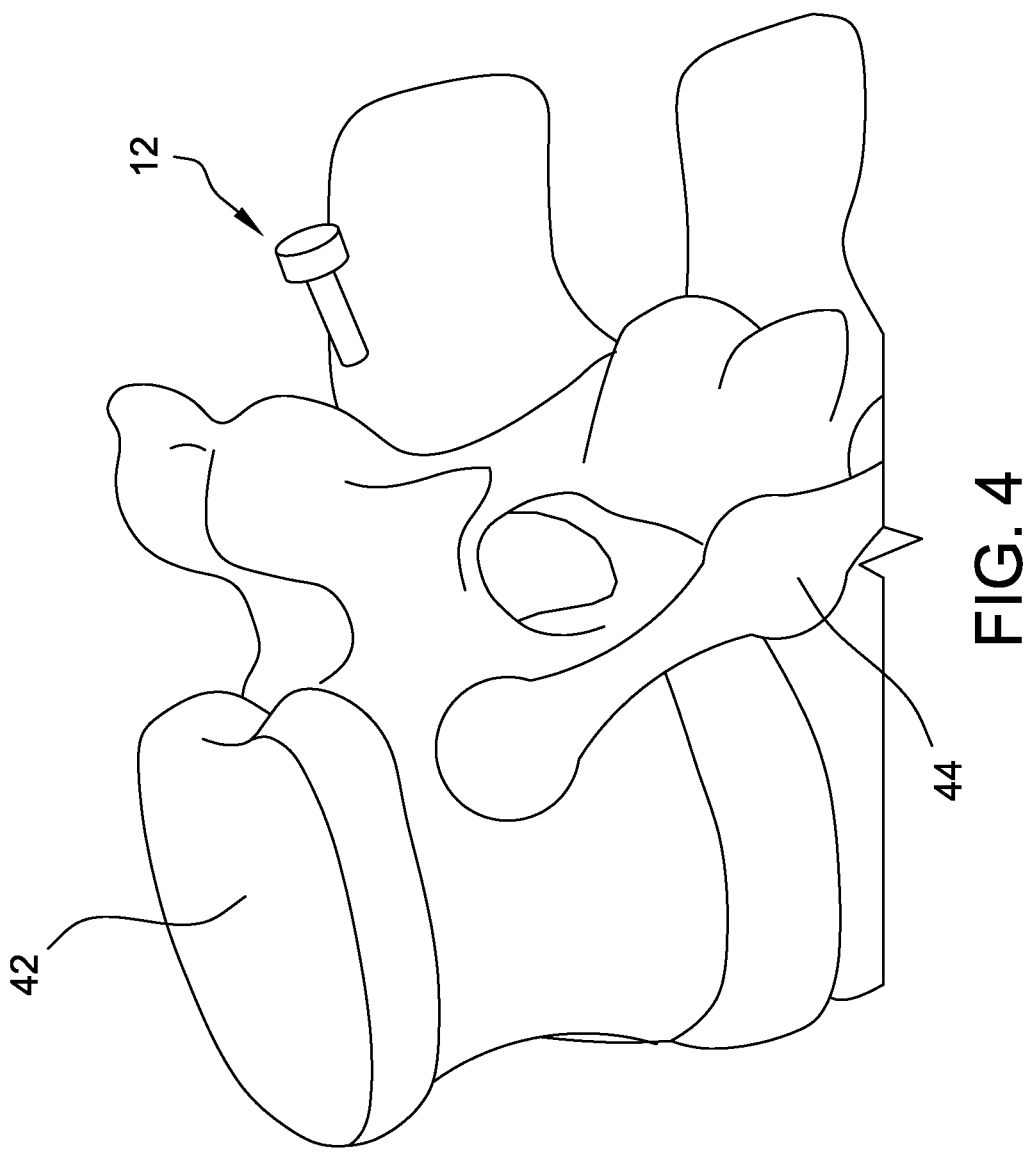
FIG. 4 is a perspective view of the electrode assembly proximate a spine and a sympathetic nerve of a human body.
Figure 5:
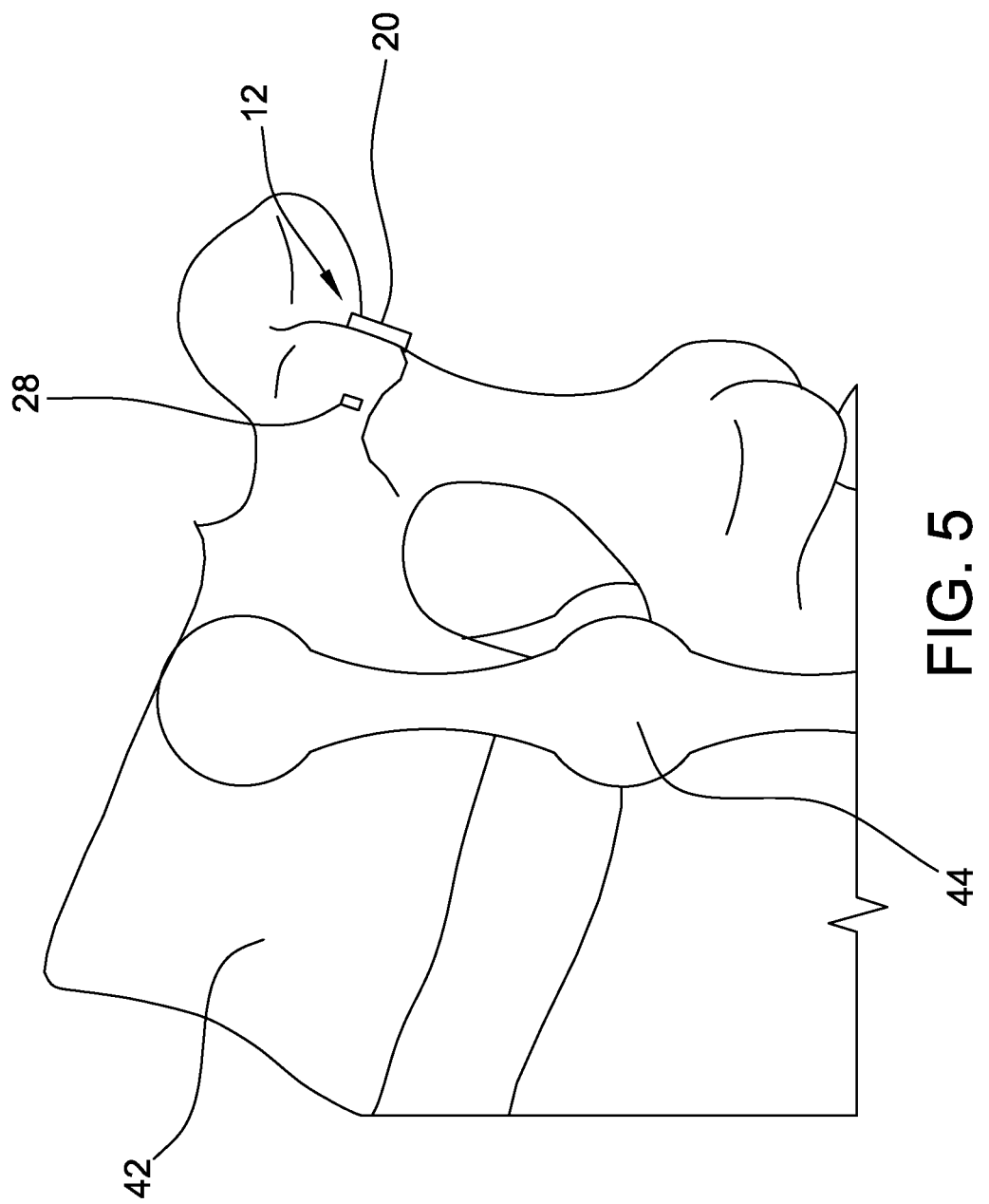
FIG. 5 is a perspective view of the electrode assembly shown in FIGS. 1-4 positioned to deliver electrical current to the sympathetic nerve shown in FIG. 4.
Figure 6:
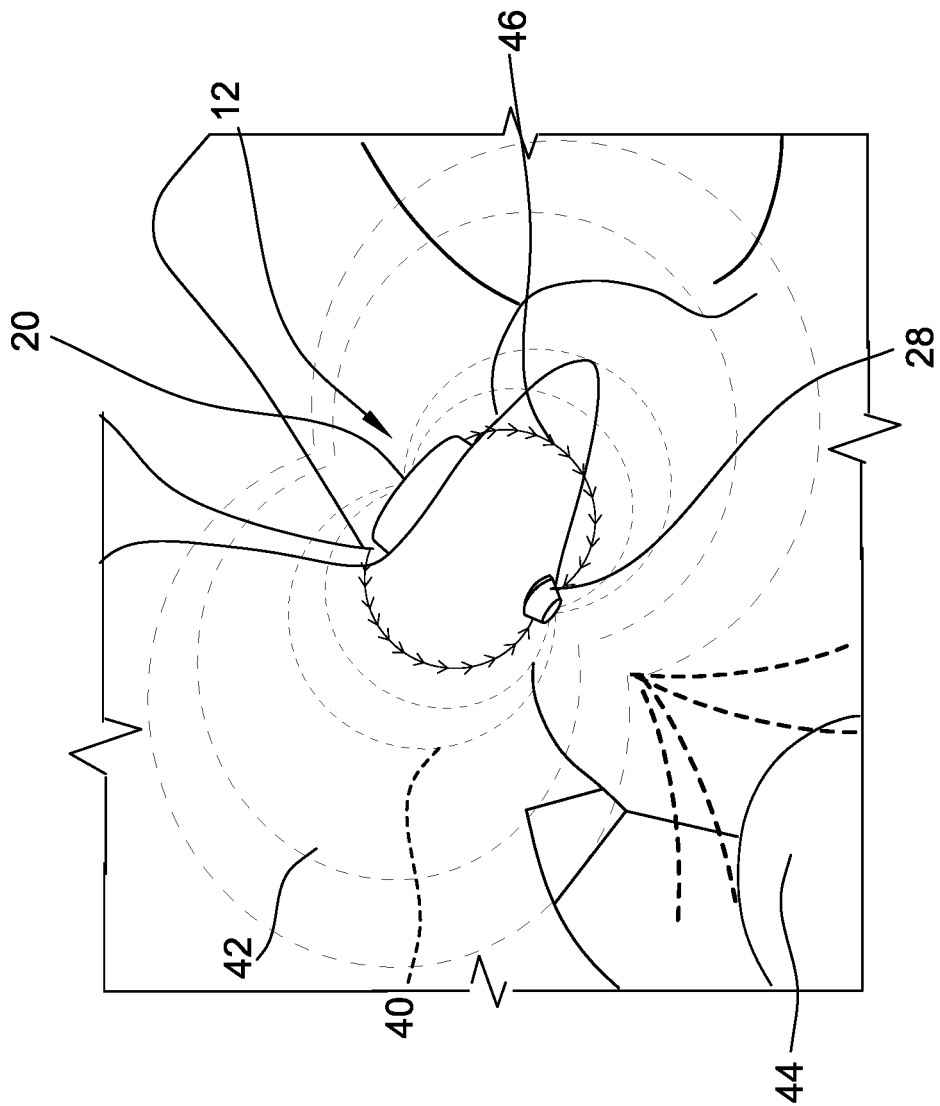
FIG. 6 is an enlarged perspective view of the electrode assembly shown in FIGS. 1-4 illustrating the flow of electrical current between an anode and cathode of the electrode.

FIG. 4 is a perspective view of the electrode assembly 12 and a spine 42 and a sympathetic chain 44 of a human body prior to the electrode assembly 12 being attached to the spine 42. FIG. 5 is a perspective view of the electrode assembly 12 positioned to deliver electrical current to the sympathetic chain 44. FIG. 6 is an enlarged perspective view of the electrode assembly 12 illustrating the flow of electrical current 46 between the anode 20 and the cathode 28 of the electrode assembly 12. The electrode assembly 12 may be attached to the spine 42 proximate the sympathetic chain 44. Accordingly, the electrical field 40 reaches the sympathetic chain 44 and the electrode assembly 12 is positioned to deliver electrical stimulation to the sympathetic chain 44.

In the illustrated embodiment, the electrode assembly 12 delivers therapeutic electrical pulses to targeted portions of the sympathetic chain 44 within the body. Accordingly, the electrode assembly 12 may be used for treatment of, for example and without limitation, sympathetic nerve dysfunction, damage to the sympathetic chain 44, and/or neuropathy pain. In suitable embodiments, the system 10 may be configured for stimulating any tissue. For example, in suitable embodiments, the electrode assembly 12 may deliver electrical pulses to boney tissue and/or soft tissue including, without limitation, muscles, tendons, ligaments, fascia, nerves, fibrous tissues, fat, blood vessels, synovial membranes, spinal cord, nerve roots, nerve root ganglion, facets, and joints. In suitable embodiments, the electrode assembly 12 may be used for modification of tissue function.

The electrode assembly 12 may be used to deliver electrical stimulation to the targeted sympathetic chain 44 according to a treatment plan. In suitable embodiments, the smallest unit of the waveform, which is the pulse shape, may be the same for multiple treatment plans. Parameters of the stimulation such as the pulse width, pulse amplitude, pulse frequency, and electrode location may vary in different treatment plans. Moreover, the treatment plans may deliver stimulation at intervals and each distinct stimulation session may have any suitable duration. In addition, the different treatment plans may have different numbers of stimulation sessions per a designated period such as a day. Also, the duration, e.g., days, weeks, and months, of therapy may vary in different treatment plans.

For example, a treatment plan may include delivering specified electrical pulses at regular intervals such as daily. In suitable embodiments, the electrode assembly 12 may provide electrical current having a frequency of about 2 hertz (Hz) to about 100 Hz to excite the sympathetic chain 44. The electrode assembly 12 may provide electrical current having a frequency of about 100 hertz (Hz) to about 200 Hz to inhibit the sympathetic chain 44. Also, in suitable embodiments, a treatment plan may include stimulation comprised of square biphasic current pulses which are applied at a predetermined frequency. Each pulse has a predetermined pulse width and amplitude. A constant-current square-pulse provides an efficient way to charge, and eventually excite, the target tissue. In addition, the pulses are biphasic which prevents a DC charge build-up on the capacitive surface. In further embodiments, the electrical stimulation may be delivered according to any suitable treatment plan.

The controller 36 (shown in FIG. 1) may be configured to automatically control the electrode assembly 12 according to the treatment plan. In further embodiments, the electrode assembly 12 is at least partially controlled based on user inputs.

As seen in FIG. 6, the electrode assembly 12 may be secured to a prominent bone proximate the sympathetic chain 44 and deliver electrical pulses to the sympathetic chain 44. For example, the electrode assembly 12 may be secured on a transverse process in the lumbar portion of the spine 42 and/or on a rib head in the thoracic region of the spine 42. The sympathetic ganglia of the sympathetic chain 44 runs along the sagittal axis of the spine 42 and is proximate such locations. Suitably, the electrode assembly 12 is secured to a prominent bone and located within about 2 mm to about 4 mm of the sympathetic ganglia. Accordingly, the electrode assembly 12 may be securely attached to the spine 42 in a precise position relative to the sympathetic chain 44 and may remain in the body as a permanent implant. In addition, the electrode assembly 12 is spaced from the sympathetic chain 44 and does not contact the sympathetic chain 44. As a result, the electrode assembly 12 is able to provide electrical stimulation to the sympathetic chain 44 without direct physical contact with the sympathetic chain 44. In other embodiments, the electrode assembly 12 may be secured to the body in any manner that enables the electrode assembly 12 to function as described herein.

Figure 7:
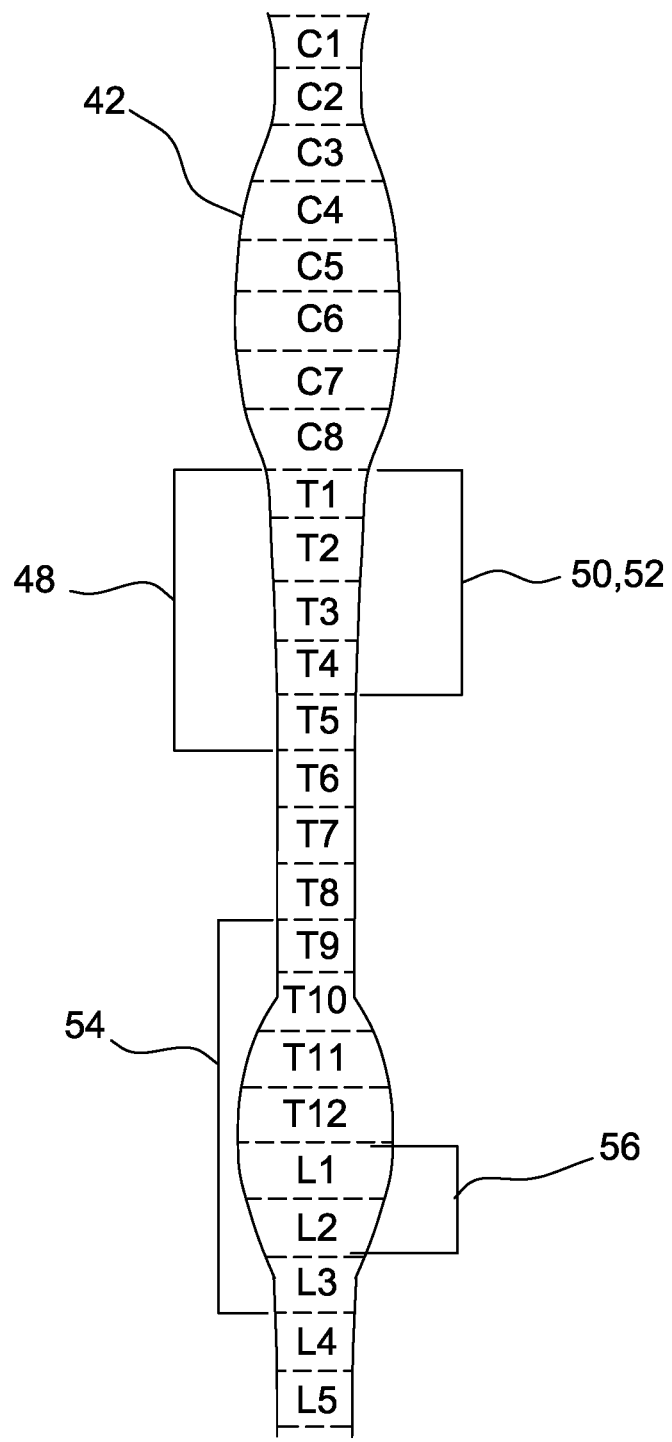
FIG. 7 is a schematic view of a sympathetic chain.

FIG. 7 is a schematic view of the sympathetic chain 44. The sympathetic chain 44 extends along the spine 42. The sympathetic chain 44 includes regions 48, 50, 52, 54, and 56 that are associated with control of certain organs and/or with conditions of the human body. For example, a first region 48 is associated with asthma. A second region 50 is associated with hypertension. A third region 52 is associated with hyperhidrosis. A fourth region 54 is associated with gastrointestinal diseases. A fifth region 56 is associated with an overactive bladder. Accordingly, therapeutic treatment of regions 48, 50, 52, 54, and 56 may affect the respective associated conditions. Specifically, excitation of region 48 may alleviate asthma. Inhibition of respective regions 50, 52, 54, and 56 may alleviate hypertension, hyperhidrosis, gastrointestinal diseases, and overactive bladder. However, at least some regions 48, 50, 52, 54, and 56 of the sympathetic chain 44 at least partially overlap each other. Accordingly, therapeutic treatment of a condition associated with one of regions 48, 50, 52, 54, and 56 must be precisely delivered to the respective region 48, 50, 52, 54, and 56 to prevent unintended affects to other regions 48, 50, 52, 54, and 56 of the sympathetic chain 44. In addition, the electrical stimulation must be precisely controlled to prevent damage to the sympathetic chain 44 in the targeted region and/or adjacent regions because damaging the sympathetic nerve 44 can cause organ dysfunction and conditions associated with dysfunction of the sympathetic chain 44. Suitably, the electrode assembly 12 described herein may be precisely positioned relative to the sympathetic chain 44 and deliver therapeutic electrical pulses to the sympathetic chain 44 without contacting the sympathetic chain 44.

With reference to FIGS. 1-7, a method of stimulating sympathetic nerves includes positioning the electrode assembly 12 at a treatment location within a body. The electrode assembly 12 may be implanted within a human body and positioned during a surgical procedure. Specifically, the electrode assembly 12 may be secured to the spine 42 proximate a targeted region 48, 50, 52, 54, 56 of the sympathetic chain 44. The power supply 34 and/or controller 36 may also be implanted within the body. Any incisions in the body may be closed and repaired after the system 10 is implanted within the body. Accordingly, the system 10 allows for stimulation after the surgical procedure is completed and, in contrast to some nerve stimulation systems, the treatment is not limited to only during the surgical procedure.

During a treatment interval, the power supply provides electrical current to the electrode assembly 12 and the electrode assembly 12 generates an electrical field 40 between the anode 20 and the cathode 28. The controller 36 may control the electrical current to cause the electrical field to deliver therapeutic electrical pulses having specified pulse duration to the sympathetic chain 44 during a treatment interval. The controller 36 may repeat the treatment intervals according to a treatment plan until the end of the treatment plan and/or the end of the service life of the electrode assembly 12. After completion of the treatment plan and/or the end of the service life of the electrode assembly 12, the electrode assembly 12 may be removed from the body. In suitable embodiments, the electrode assembly 12 may remain in the body as a permanent implant. In further embodiments, portions of the system 10 such as the power supply 34 may be replaceable to prolong the service life of the system 10.

Figure 8:
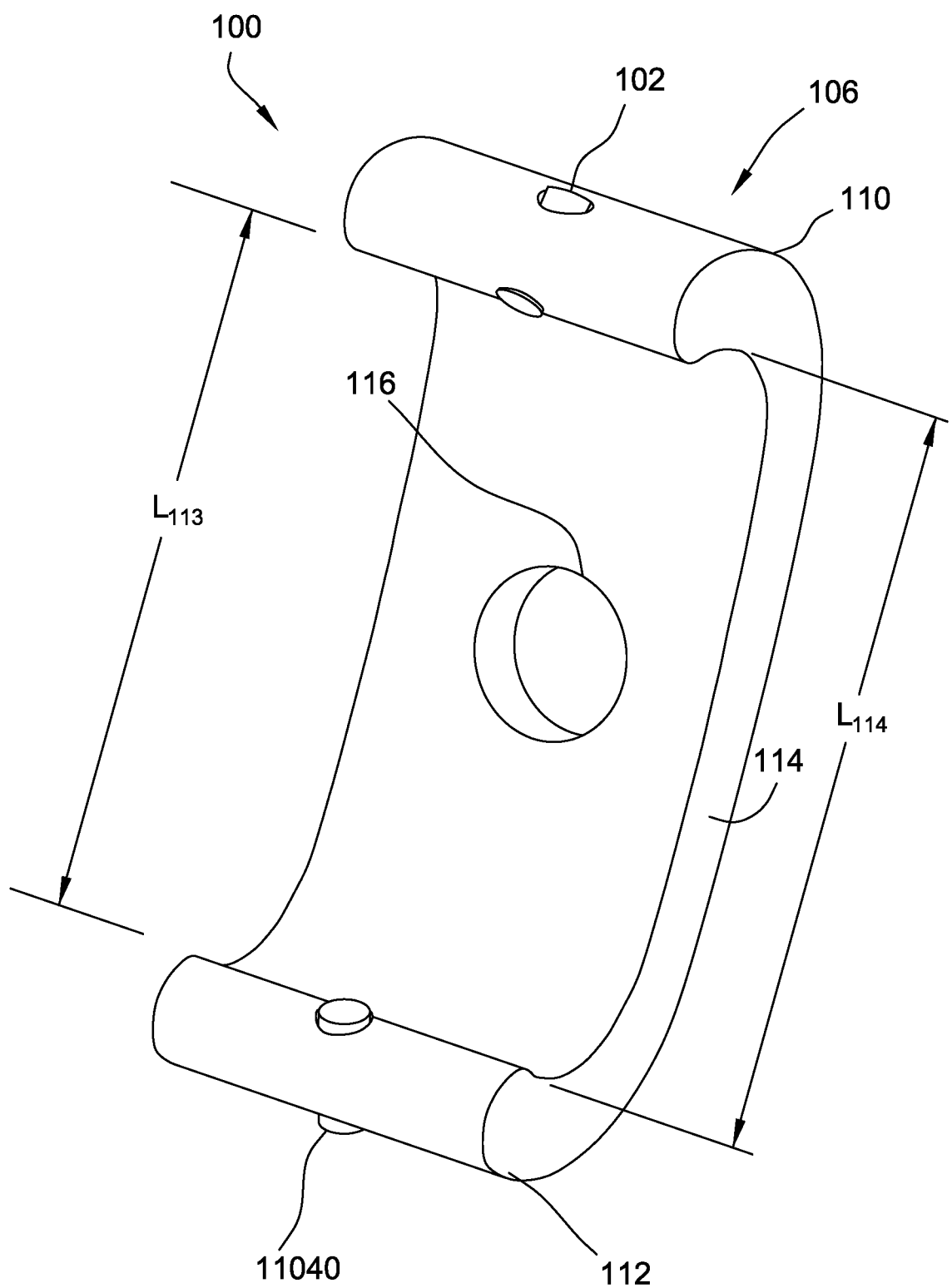
FIG. 8 is a perspective view of a suitable embodiment of an electrode assembly for use with the system shown in FIG. 1, the electrode assembly including a support structure.
Figure 9:
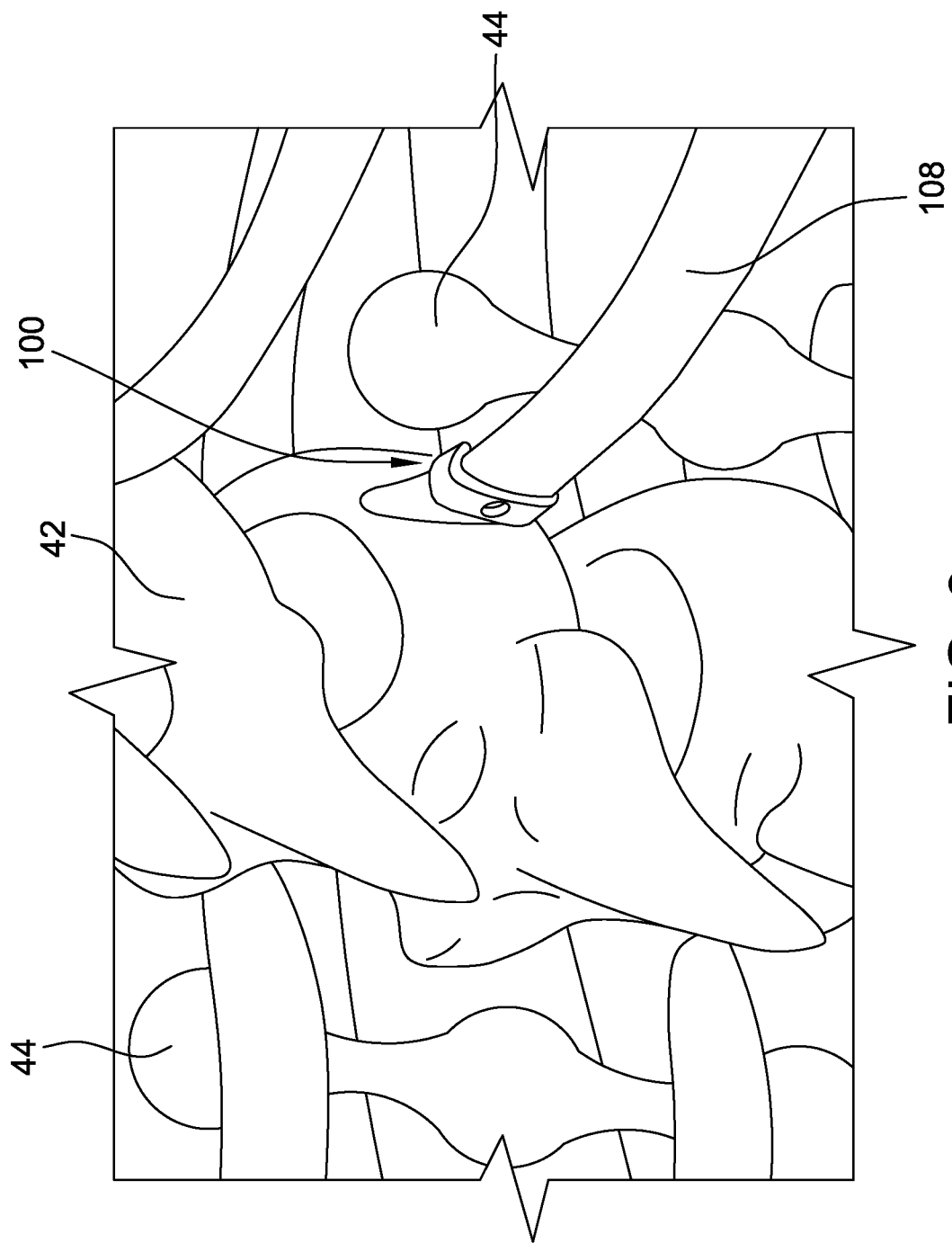
FIG. 9 is a perspective view of the electrode assembly shown in FIG. 8 positioned to deliver electrical current to a sympathetic chain of a human body.

FIG. 8 is a perspective view of an electrode assembly 100 for use with the system 10 (shown in FIG. 1). FIG. 9 is a perspective view of the electrode assembly 100 positioned to deliver electrical current to a sympathetic chain 44 of a human body. Electrode assembly 100 includes a first electrode 102, a second electrode 104, and a support structure 106. The support structure 106 is shaped and sized to attach to a bone such as a rib 108 of the human body proximate the sympathetic chain 44. The support structure 106 includes a first end 110, a second end 112, and a middle 114. The middle 114 extends between the first end 110 and the second end 112 and is substantially planar. The first end 110 and the second end 112 are curved relative to the middle 114 and are configured to extend over edges of a bone. The middle 114 has a length $L_{114}$. The first electrode 102 is attached to the first end 110 and the second electrode 104 is attached to the second end 112. Accordingly, the first electrode 102 and the second electrode 104 are spaced apart by the length $L_{113}$ of the middle 114. The middle 114 defines an opening 116 to receive a fixation screw (not shown) for securing the electrode assembly 100 to the bone. In other embodiments, the support structure 106 may have any configuration that enables the electrode assembly 100 to operate as described herein. For example, in some embodiments, the electrode assembly 100 may be fixed to the bone without using a fixation screw.

The electrode assembly 100 generates an electrical field between the first electrode 102 and the second electrode 104 and provides therapeutic pulses to a targeted portion of the sympathetic chain 44 according to a treatment plan. In suitable embodiments, the electrode assembly 100 may be configured to provide unidirectional stimulation to the sympathetic nerve. In other embodiments, the electrode assembly 100 may be configured to deliver any current to the tissue that enables the system 10 (shown in FIG. 1) to operate as described herein.

Figure 10:
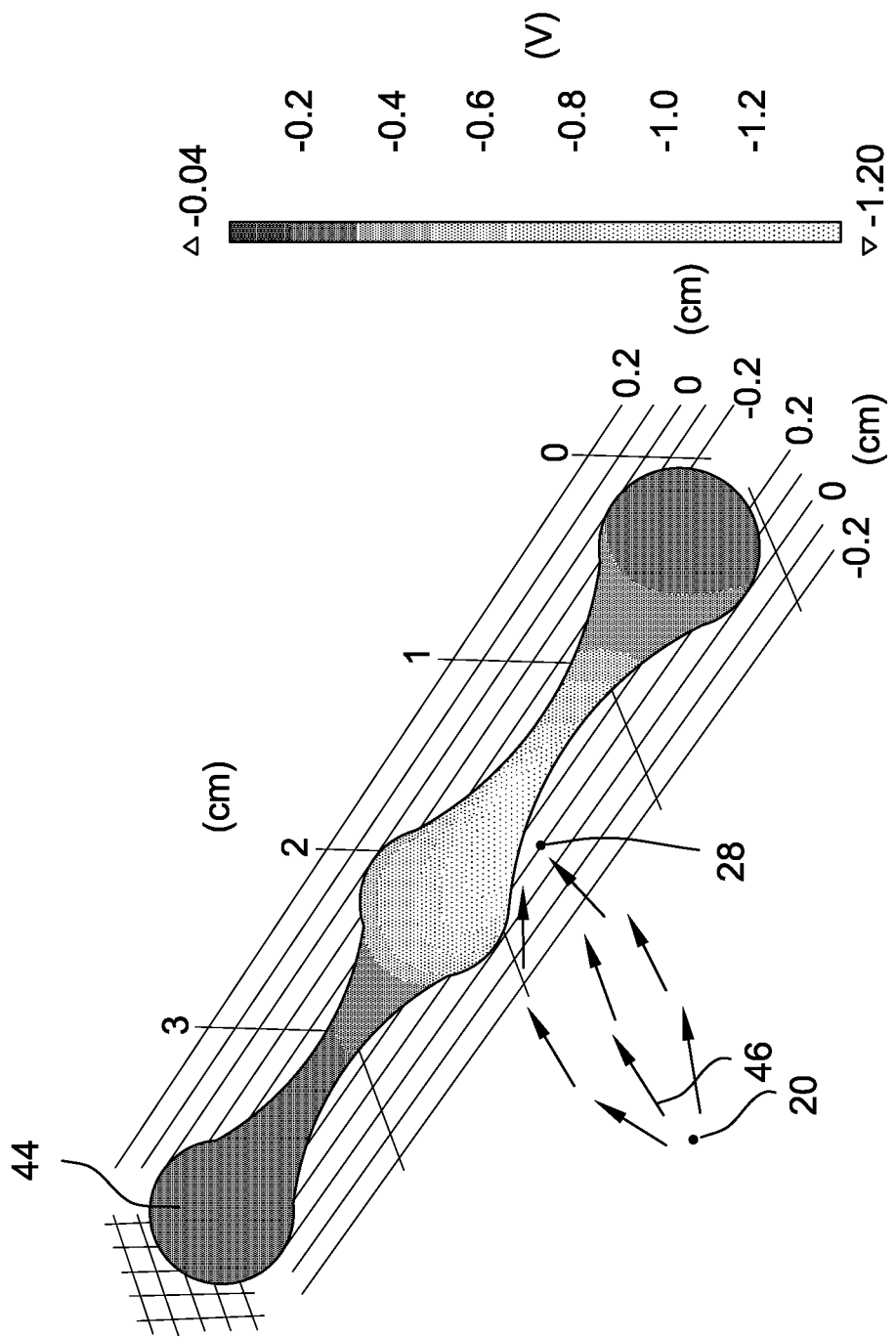
FIG. 10 is a graph of electrical potential distribution on a surface of the sympathetic chain.

FIG. 10 is a graph of electrical potential distribution in volts (V) on a surface of the sympathetic chain 44 plotted in centimeters (cm). The electrical potential distribution is based on the electrical field 40 generated between the cathode 28 and anode 20 when the electrode assembly 12 is positioned proximate the sympathetic chain 44 and an electrical current having an amplitude less than 10 mA is supplied to the electrode assembly 12. In the model configuration, the cathode 28 is positioned approximately 4 mm from the sympathetic chain 44.

Figure 11:
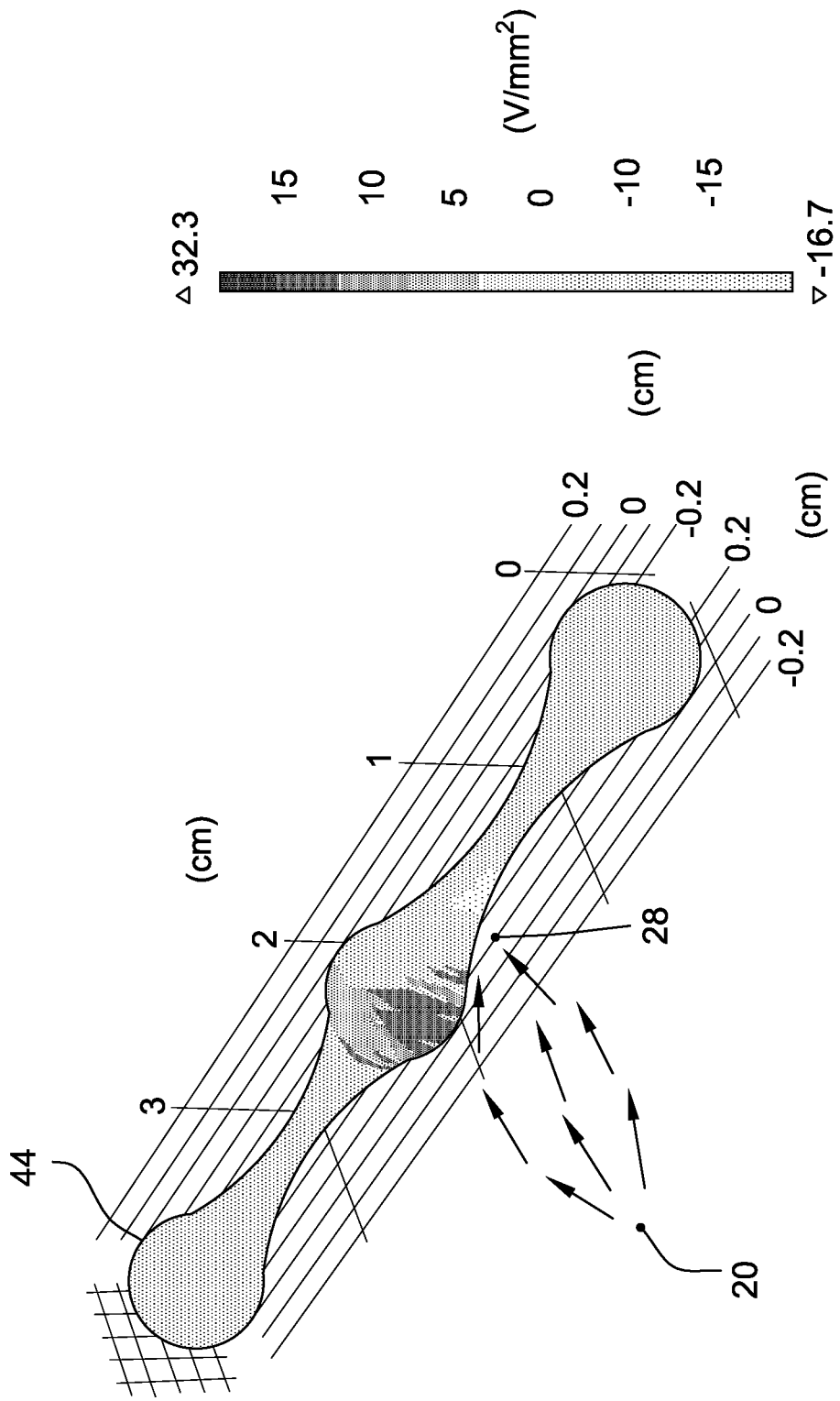
FIG. 11 is a graph of the distribution of the second spatial derivative of the electrical potential shown in FIG. 10.

FIG. 11 is a graph of the distribution of the second spatial derivative of the electrical potential shown in FIG. 10 on the sympathetic chain 44 using units of volts per millimeter$^2$ ($V/mm^2$). The second spatial derivative is proportional to the influence of the electrical field 40 on an axon or neuron of the sympathetic chain 44. Accordingly, the second spatial derivative can be used to determine characteristics of the activating function of the sympathetic chain 44. The second spatial derivative is greater than zero at points where the electrical field 40 would influence the sympathetic chain 44. In addition, the second spatial derivative shows that the influence is cathodal. Accordingly, the modeled configuration of the electrical field 40 relative to the sympathetic chain 44 demonstrates potential for stimulation of the sympathetic chain 44.

Figure 12:
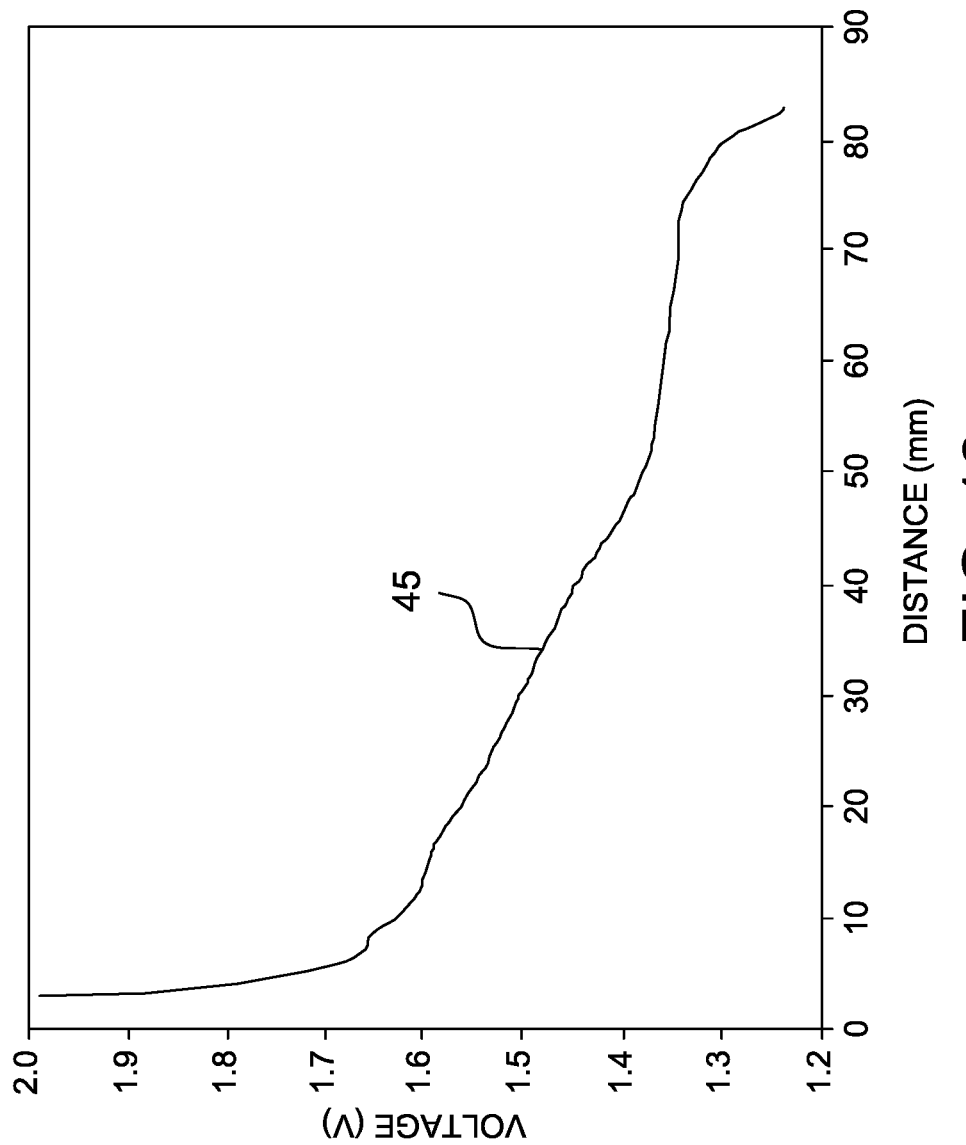
FIG. 12 is a graph comparing voltage to distance for an electrical field generated by the electrode assembly shown in FIG. 1.

FIG. 12 is a graph of experimental measures of voltage (V) of the electric field 40 (shown in FIGS. 10 and 11) at various distances (mm) generated by the electrode assembly 12 (shown in FIG. 1). A curve 45 represents the voltage-distance relationship between the electrode assembly 12 and a stimulated component, such as the sympathetic chain 44 (shown in FIGS. 10 and 11). Specifically, the curve 45 represents the distance between the cathode 28 and the stimulated component. The voltage decreases as the distance between the electrode assembly 12 and the sympathetic chain 44 increases. Voltages generated at various distances from the electrode assembly follow Coulomb's law. Accordingly, electrical stimulation may be generated at targeted locations along the sympathetic chain 44 by strategic placement of the electrode assembly 12 at specified distances from the sympathetic chain 44.

Example

Experimental testing was conducted to evaluate the capability of the system 10 to provide electrical stimulation to nervous tissue. Operations were performed on a test subject, specifically a rat, to expose nervous tissue and provide electrical stimulation to the nervous tissue. Specifically, electrical stimulation was provided to the rat using the electrode assembly 12 positioned proximate the sciatic nerve. The electrode assembly 12 did not contact the sciatic nerve and was positioned approximately 3 mm away from the sciatic nerve with a layer of soft tissue between the sciatic nerve and the electrode assembly 12. Electrical current having an amplitude of approximately 0.8 milliamps (mA) was provided to the electrode assembly 12. The electrical current was provided for a first period at a frequency of 20 Hz and for a second period at a frequency of 50 Hz. The muscle contractions of the rat's leg muscle, which is controlled by the sciatic nerve, were measured using electromyography (EMG) signals.

Figure 13:
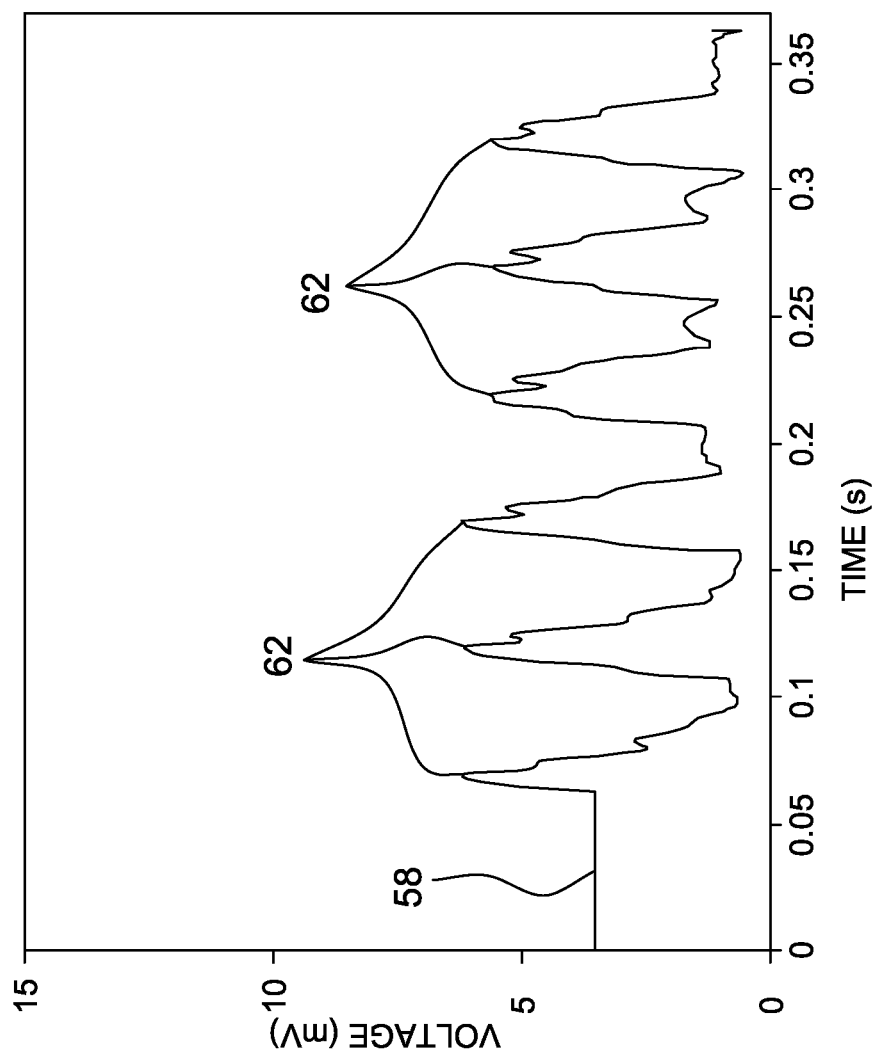
FIG. 13 is a graph of electromyography (EMG) signals measured in tissue of a test subject electrically stimulated with a current having a frequency of 20 Hz.
Figure 14:
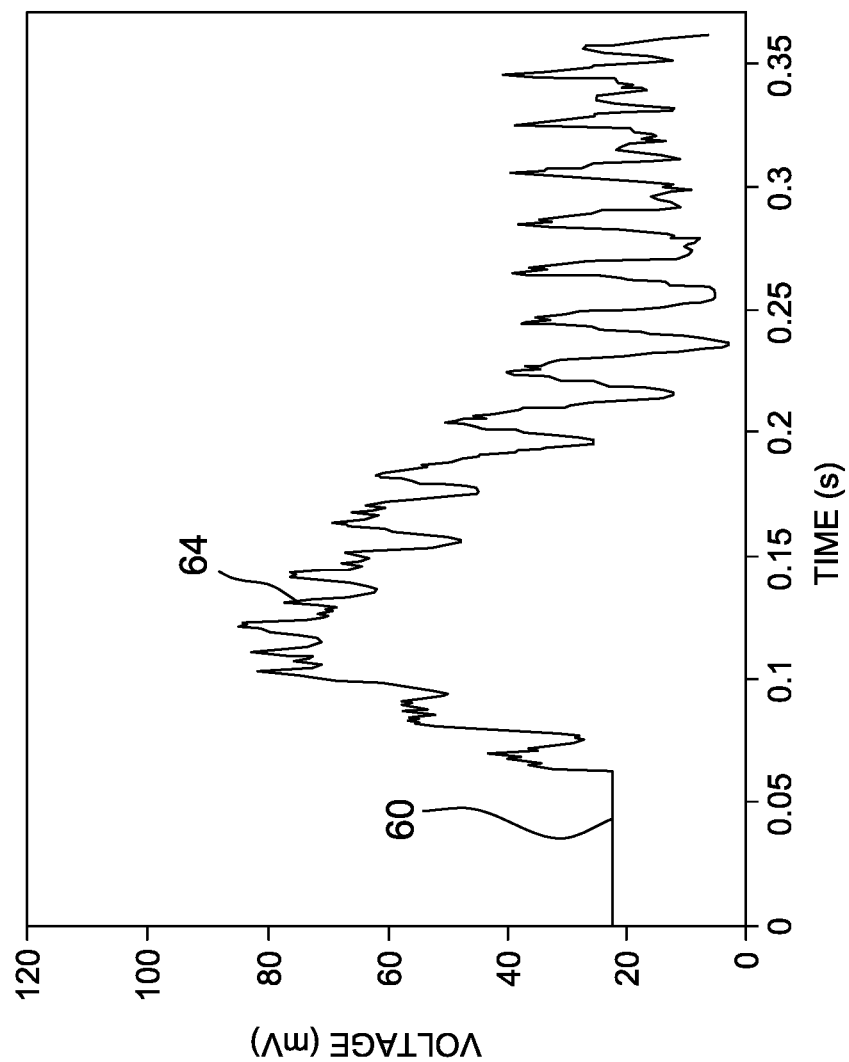
FIG. 14 is a graph of EMG signals measured in tissue of a test subject electrically stimulated with a current having a frequency of 50 Hz.

FIGS. 13 and 14 are graphs of voltage versus time based on the EMG signals measured in the test subject's leg muscle. FIG. 13 includes a curve 58 representing EMG signals measured in the rat's leg muscle in response to a current having a frequency of 20 Hz. The curve 58 includes detectable individual muscle contractions 62 which indicate twitch contractions in the leg muscle. FIG. 14 includes a curve 60 representing EMG signals measured in the rat's leg muscle in response to a current having a frequency of 50 Hz. Stimulation at the higher frequency resulted in tetanic muscle contractions, in which individual muscle contractions occur rapidly without complete relaxation between twitches, resulting in tetanus. Accordingly, the experimental tests demonstrated that the test subject had a measurable response to electrical stimulation to the nervous tissue using the system 10 without the electrode assembly 12 contacting the nervous tissue. In addition, the electrical current supplied at different frequencies generated different responses in the treated tissue. Accordingly, electrical pulses with different frequencies may be provided to nervous tissue to modulate behavior of the tissue.

Embodiments of the tissue stimulation system allow electrical pulses to be applied to nervous tissue to stimulate a targeted portion of the sympathetic chain. For example, the systems may provide controlled pulses of electrical stimulation to targeted treatment locations of the sympathetic chain without direct physical contact with the sympathetic chain. The system may include an electrode assembly that is secured to a prominent bone structure proximate the sympathetic chain. Accordingly, the electrode assembly may be more easily implanted within the body of the animal than a system requiring contact with the tissue. In addition, the electrode assembly may reduce the risk of damage to the sympathetic chain because the electrode does not contact the sympathetic chain.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method of stimulating a sympathetic chain of a patient, the method comprising:
   adjusting a length of an electrode assembly by manipulating an end portion of the electrode;
   fixating the electrode assembly to a bone in proximity to a targeted portion of the sympathetic chain to inhibit movement of the electrode assembly relative to the bone, the electrode assembly including a cathode and an anode, wherein a distance between the anode and the cathode is selectable by the adjusting of the length of the electrode assembly;
   connecting a power supply to the electrode assembly, the power supply configured to deliver power to the electrode assembly; and
   delivering power to the electrode assembly to generate an electrical field between the cathode and the anode, wherein the electrical field reaches the targeted portion of the sympathetic chain to provide electrical stimulation to the targeted portion of the sympathetic chain.

2. The method of claim 1, wherein the electrode assembly does not directly contact the sympathetic chain when fixated to the bone.

3. The method of claim 1, wherein fixating the electrode assembly to the bone comprises attaching the electrode assembly to a bone of a spine proximate the sympathetic chain.

4. The method of claim 3, wherein attaching the electrode assembly to the bone of the spine proximate the sympathetic chain comprises attaching the electrode assembly to a transverse process in a lumbar portion of the spine.

5. The method of claim 3, wherein attaching the electrode assembly to the bone of the spine proximate the sympathetic chain comprises attaching the electrode assembly to a rib head in a thoracic region of the spine.

6. The method of claim 1, wherein fixating the electrode assembly to the bone comprises fixating the electrode assembly to the bone at a location that is 2 mm to 4 mm from a sympathetic ganglia of the sympathetic chain.

7. The method of claim 1, further comprising connecting wires to the anode and the cathode and connecting the wires to the power supply.

8. The method of claim 1, further comprising regulating, by a controller connected to the power supply, electrical current provided to the electrode assembly.

9. The method of claim 8, wherein regulating, by the controller connected to the power supply, the electrical current comprises regulating a parameter of the electrical current selected from a group consisting of pulse width, pulse amplitude, pulse frequency, current, and stimulation interval.

10. The method of claim 8, further comprising applying, by the electrode assembly, square biphasic current pulses at a predetermined frequency.

11. The method of claim 1, wherein fixating the electrode assembly to the bone in proximity to the targeted portion of the sympathetic chain comprises fixating the electrode assembly to the bone in proximity to a targeted portion of the sympathetic chain associated with hypertension.

12. The method of claim 1, wherein fixating the electrode assembly to the bone in proximity to the targeted portion of the sympathetic chain comprises fixating the electrode assembly to the bone in proximity to a targeted portion of the sympathetic chain associated with gastrointestinal diseases.

13. The method of claim 1, wherein fixating the electrode assembly to the bone in proximity to the targeted portion of the sympathetic chain comprises fixating the electrode assembly to the bone in proximity to a targeted portion of the sympathetic chain associated with urological disorders.

14. The method of claim 1, wherein fixating the electrode assembly to the bone in proximity to the targeted portion of the sympathetic chain comprises fixating the electrode assembly to the bone in proximity to a targeted portion of the sympathetic chain associated with an overactive bladder.

15. A method of stimulating a sympathetic chain of a patient, the method comprising:
fixating an electrode assembly to a bone in proximity to a targeted portion of the sympathetic chain to inhibit movement of the electrode assembly relative to the bone, the electrode assembly including a cathode, an anode, and a support structure, the support structure having a first end, a second end, and a middle portion disposed between the first end and the second end, the first end and the second end being curved relative to the middle portion to extend over edges of the bone;
connecting a power supply to the electrode assembly, the power supply configured to deliver power to the electrode assembly; and
delivering power to the electrode assembly to generate an electrical field between the cathode and the anode when power is delivered to the electrode assembly, and wherein the electrical field reaches the targeted portion of the sympathetic chain to provide electrical stimulation to the targeted portion of the sympathetic chain.

16. The method of claim 15, wherein the electrode assembly does not directly contact the sympathetic chain when fixated to the bone.

17. The method of claim 15, wherein fixating the electrode assembly to the bone comprises attaching the electrode assembly to a bone of a spine proximate the sympathetic chain.

18. The method of claim 17, wherein attaching the electrode assembly to the bone of the spine proximate the sympathetic chain comprises attaching the electrode assembly to a transverse process in a lumbar portion of the spine.

19. The method of claim 17, wherein attaching the electrode assembly to the bone of the spine proximate the sympathetic chain comprises attaching the electrode assembly to a rib head in a thoracic region of the spine.

20. The method of claim 15, wherein fixating the electrode assembly to the bone comprises fixating the electrode assembly to the bone at a location that is 2 mm to 4 mm from a sympathetic ganglia of the sympathetic chain.

21. The method of claim 15, further comprising regulating, by a controller connected to the power supply, the electrical current comprises regulating a parameter of the electrical current selected from a group consisting of pulse width, pulse amplitude, pulse frequency, current, and stimulation interval.

22. The method of claim 1, wherein the length is selectable between about 4 millimeters (mm) to about 22 mm.

23. The method of claim 1, wherein manipulating the end portion further comprises rotating the end portion.

24. The method of claim 23, wherein the end portion includes threads that mate with further comprises rotating the end portion.

* * * * *